United States Patent [19]

Gupta

[11] Patent Number: 5,631,386
[45] Date of Patent: May 20, 1997

[54] ALKYLENE CARBONATE RECOVERY

[75] Inventor: Vijai P. Gupta, Berwyn, Pa.

[73] Assignee: ARCO Chemical Technology, L.P., Greenville, Del.

[21] Appl. No.: 691,665

[22] Filed: Aug. 2, 1996

[51] Int. Cl.$^6$ .............. C07D 317/36; C07D 317/38; C07D 321/06; C07D 319/06
[52] U.S. Cl. ............................. 549/228; 549/230
[58] Field of Search ........................ 549/230, 228

[56] References Cited

U.S. PATENT DOCUMENTS

| | | | |
|---|---|---|---|
| 2,773,070 | 12/1956 | Lichtenwalter et al. | 260/340.2 |
| 2,873,282 | 2/1959 | McClellan | 260/340.2 |
| 4,786,741 | 11/1988 | Sachs | 549/230 |
| 5,179,214 | 1/1993 | Marquis et al. | 549/230 |
| 5,283,356 | 2/1994 | Marquis et al. | 558/260 |

*Primary Examiner*—Philip I. Datlow
*Assistant Examiner*—Sabiha N. Qazi
*Attorney, Agent, or Firm*—William C. Long

[57] ABSTRACT

The residual level of alkylene oxide in the reaction mixture resulting from reaction of alkylene oxide with carbon dioxide to form alkylene carbonate is reduced by stripping with an inert gas such as carbon dioxide.

4 Claims, No Drawings

ALKYLENE CARBONATE RECOVERY

BACKGROUND OF THE INVENTION

1. Field of the Invention

The present invention relates to the production of alkylene carbonate, and especially to the removal of residual alkylene oxide from the alkylene carbonate by inert gas stripping.

2. Description of the Prior Art

It is known to form an alkylene carbonate by the reaction of an alkylene oxide with carbon dioxide. See, for example, U.S. Pat. Nos. 2,773,070, 2,873,282, 4,786,741, 5,179,214, 5,283,356 and the like. Appropriate catalysts and reaction conditions are known and taught, for example, in the above references.

A problem which has been associated with prior practices has been contamination of the product alkylene carbonate with unreacted alkylene oxide. One method heretofore employed for reducing the alkylene oxide level in product alkylene carbonate has been to continue the reaction between alkylene oxide and carbon dioxide until the alkylene oxide is essentially consumed. However these procedures involve excessive reaction times since the reaction slows considerably at low alkylene oxide concentrations.

It has been proposed, for example in U.S. Pat. Nos. 5,179,214 and 5,283,356 that in a continuous reaction system the alkylene oxide and carbon dioxide be introduced into a continuous reactor containing catalyst with continuous recirculation of a portion of the reaction mixture and continuous withdrawal and flashing of another portion of the reaction mixture to remove unreacted alkylene oxide and carbon dioxide; the removed materials can be compressed and returned to the reaction mixture. The residue from flashing is distilled to separate product carbonate from the catalyst solution. These procedures are not effective in reducing the level of unreacted alkylene oxide in the alkylene carbonate sufficiently without the necessity of elaborate and expensive distillation procedures. A problem in continuous systems has been that higher temperatures are employed than in batch systems in order to reduce unreacted alkylene oxide levels but this has the disadvantage of forming light and heavy impurities. Elaborate alkylene oxide distillation procedures are required to produce satisfactory product.

BRIEF DESCRIPTION OF THE INVENTION

It has now been found that residual alkylene oxide levels in the product alkylene carbonate can be reduced to a satisfactorily low figure by stripping alkylene oxide from the alkylene carbonate by passing an inert stripping gas such as carbon dioxide through the alkylene oxide containing alkylene carbonate until the alkylene oxide concentration is reduced to a satisfactorily low level.

DETAILED DESCRIPTION

In practice of the invention, known reagents, catalyst and reaction conditions are employed. See, for example, U.S. Pat. Nos. 2,773,070, 2,873,282, 4,786,741, 5,179,214, 5,283,356 and the like, the disclosures of which are incorporated herein by reference.

The invention is especially applicable to the production of propylene carbonate and ethylene carbonate by the tetraethyl ammonium bromide catalyzed reaction of propylene oxide with carbon dioxide and ethylene oxide with carbon dioxide.

As described in U.S. Pat. No. 5,283,356, the reaction of an alkylene oxide and carbon dioxide to form alkylene carbonate may be carried out at a temperature of from about 100° to about 225° C. or higher, preferably from about 175° to about 215° C. The reaction may be carried out at atmospheric pressure or, advantageously, under a pressure of about 300 psig or greater. More preferably, the reaction is carried out under a pressure of about 300 to about 3000 psig. The reaction may be conducted either batch-wise or continuously.

In a continuous reaction, the alkylene oxide and carbon dioxide are introduced to a continuous reactor containing the catalyst, from which a portion of the reaction mixture may be continuously recirculated through the reactor. Another portion of this reaction mixture is continuously withdrawn and treated in accordance with the invention to remove unreacted alkylene oxide from product alkylene carbonate. Alternatively, the continuous reaction can be carried out on a once through basis with suitable heat removal.

Alternatively, batches of the alkylene oxide and catalyst may be introduced into an autoclave or kettle type reactor. The desired pressure may be built up by introducing carbon dioxide. Typically, the reaction mixture is heated to reaction temperature, agitated, and held under a superatmospheric pressure of carbon dioxide. After the bulk of the alkylene oxide has reacted, the reaction mixture is treated in accordance with the invention to remove unreacted alkylene oxide.

The alkylene oxide and carbon dioxide should be mixed in proportion to provide an excess of carbon dioxide over and above the stoichiometric amount required for reaction. This excess may be on the order of from about 1.1 moles of carbon dioxide per mole of alkylene oxide to about 10 moles of carbon dioxide per mole of alkylene oxide. An excess of alkylene oxide should be avoided, because it results in undesired by-products, chiefly alkylene oxide polymer, and because explosive conditions may result.

In accordance with the present invention, after completion of the desired reaction between the alkylene oxide and carbon dioxide to form alkylene carbonate, the reaction mixture is treated to remove residual unreacted alkylene oxide. Advantageously, the system pressure is reduced and carbon dioxide and alkylene oxide are vented from the system. Even after such venting the reaction mixture contains unacceptable levels of alkylene oxide, usually from 0.1% to 1% or more as against acceptable levels of 0.06% or less. Simple flashing and removal of flashed alkylene oxide and carbon dioxide is generally ineffective in producing acceptable product.

In certain past practices, the alkylene oxide and carbon dioxide reaction has been continued until the residual alkylene oxide is 0.06% or less but this procedure takes an inordinate amount of time. For example, in batch reactions it takes about as long a reaction time to reduce the alkylene oxide concentration from 10% to 1% as it does to reduce the concentration from 1% to 0.1%. Obviously reactor productivity is greatly reduced in past practices where the alkylene oxide was reduced to acceptable levels by reaction with carbon dioxide.

Now through the process of this invention, after the reaction has proceeded to a reasonable extent, the system can be vented, preferably the reaction mixture temperature is reduced somewhat to avoid further reactions in the system, eg. to 150° C. or so, and the reaction mixture is stripped of residual alkylene oxide by passage of an inert gas therethrough until the residual alkylene oxide level is 0.06% or less. Generally, inert gas vapor is passed through the liquid reaction mixture at the rate of 0.01 to 1.00 parts by weight of inert gas vapor per parts by weight of liquid per hour, preferably 0.02 to 0.2 parts by weight of inert gas per parts by weight of liquid per hour. Generally, stripping times of 5 to 200 minutes, preferably 10 to 100 minutes are adequate. Conventional means for introducing the vapor in finely dispersed form below the liquid level are used.

By inert gas as used herein is meant a gas which does not undergo substantial reaction with constituents of the reaction mixture at the stripping conditions. Carbon dioxide is the preferred inert stripping gas. Other inert gases such as nitrogen, argon, helium and the like can be used.

In order to more clearly illustrate the invention, reference is made to the following examples.

In each case, 100 lbs propylene oxide and 0.5 lbs tetraethyl ammonium bromide catalyst were charged to a stirred batch reactor. The mixture was heated to about 185° C. and pressured to 600 psig with carbon dioxide. After the designated reaction time, the reactor was depressurized to atmospheric pressure by venting and the reaction mixture cooled to about 150° C.

Thereafter, the reaction mixture in each case was stripped by passage there through of carbon dioxide at the rate of 7 lbs/hr. The following table shows the results obtained. Specifically, it can be seen that venting the reactor and flashing of unreacted propylene oxide and carbon dioxide is not an effective procedure for reduction of residual propylene oxide levels to the necessary 0.06% or less. Likewise, it can be seen that the residual propylene oxide concentration after flashing and venting is largely a function of the propylene oxide concentration before flashing.

The data clearly indicate that even with high residual propylene oxide levels in the reaction mixture, satisfactory reduction is achieved by carbon dioxide stripping in far less time that could be achieved in accordance with past practices. In addition, the final color of propylene carbonate produced through the invention is of superior quality. APHA color of 100 or lower are readily achievable as compared with a color of 350 or higher which results from conventional procedures.

TABLE 1

| Reaction Time, hrs. | PO$^{(1)}$ conc. % | | PO$^{(1)}$ Conc. after stripping with CO$_2$ % | | | | Final color APHA |
|---|---|---|---|---|---|---|---|
| | before vent | after vent/cool | 20 minutes | 40 minutes | 60 minutes | 80 minutes | |
| 8 | 0.13 | 0.09 | 0.05 | 0.03 | 0.02 | — | 152 |
| 8 | 0.10 | 0.10 | 0.07 | 0.06 | 0.04 | — | 141 |
| 7 | 0.27 | 0.20 | 0.07 | 0.05 | 0.03 | — | 100 |
| 7 | 0.38 | 0.31 | 0.15 | 0.05 | 0.02 | — | 88 |
| 7 | 0.36 | 0.26 | 0.11 | 0.05 | 0.03 | — | 91 |
| 6 | 0.66 | 0.58 | 0.34 | 0.19 | 0.09 | 0.05 | 78 |
| 6 | 0.60 | 0.43 | 0.32 | 0.17 | 0.07 | 0.03 | 80 |
| 6 | 0.58 | 0.50 | 0.18 | 0.02 | 0.02 | — | — |
| 6 | 0.29 | 0.27 | 0.15 | 0.08 | 0.04 | — | 92 |

$^{(1)}$Propylene oxide

I claim:

1. In a process for the production of an alkylene carbonate by reaction of an alkylene oxide with carbon dioxide, the improvement which comprises reducing the residual alkylene oxide concentration in the reaction product mixture by stripping the reaction product mixture with inert gas.

2. The process of claim 1 wherein the inert gas is carbon dioxide.

3. The process of claim 1 wherein the alkylene oxide is propylene oxide and propylene carbonate is produced.

4. The process of claim 1 wherein the inert gas is nitrogen.

* * * * *